United States Patent [19]

Chapman

[11] Patent Number: 5,703,792

[45] Date of Patent: Dec. 30, 1997

[54] THREE DIMENSIONAL MEASUREMENT OF MOLECULAR DIVERSITY

[75] Inventor: David Chapman, San Francisco, Calif.

[73] Assignee: Arris Pharmaceutical Corporation, South San Francisco, Calif.

[21] Appl. No.: 357,580

[22] Filed: Dec. 13, 1994

Related U.S. Application Data

[63] Continuation-in-part of Ser. No. 382,990, Oct. 28, 1994, Pat. No. 5,526,281, which is a continuation of Ser. No. 66,389, May 21, 1993, abandoned.

[51] Int. Cl.$^6$ .................................................. G06F 17/50
[52] U.S. Cl. .................................... 364/496; 364/578
[58] Field of Search ................................ 364/496, 497, 364/499, 578; 436/43, 8

[56] References Cited

U.S. PATENT DOCUMENTS

| | | | |
|---|---|---|---|
| 5,025,388 | 6/1991 | Cramer, III et al. | 364/496 |
| 5,167,009 | 11/1992 | Skeirik | 395/27 |
| 5,260,882 | 11/1993 | Blanco et al. | 364/499 |
| 5,265,030 | 11/1993 | Skolnick et al. | 364/496 |
| 5,574,656 | 11/1996 | Agrafiotis et al. | 364/496 X |

OTHER PUBLICATIONS

Kearsley et al. "Flexibases: A Way to Enhance the Use of Molecular Docking Methods", Journal of Computer-Aided Molecular Design v. 8 pp. 565–582, 1994.

T.A. Andrea, et al., Applications of Neural Networks in Quantitative Structure–Activity Relationship of Dihydrofolate Reductase Inhibitors, Journal of Medicinal Chemistry, vol. 34, No. 9, 1991, pp. 2824–2836.

Good, et al., Structure–Activity Relationships from Molecular Similarity Matrices, Journal of Medicinal Chemistry, vol. 36, No. 4, Feb. 19, 1993, pp. 433–438.

Aoyama, et al., Neural Networks Applied to Quantitative Structure–Activity Relationship Analysis, Journal of Medicinal Chemistry, 1990, vol. 33, No. 9, pp. 2583–2590.

Aoyama, et al., Obtaining the Correlation Indices Between Drug Activity and Structural Parameters Using a Neural Network, Chemical Pharmaceutical Bulletin, vol. 39, No. 2, pp. 372–378, 1991.

Oinuma, et al., Neural Networks Applied to Structure–Activity Relationships, Journal of Medicinal Chemistry, vol. 33, No. 3, 1990, pp. 905–908.

Viswanadhan, et al., Mapping the Binding Site of the Nucleoside Transporter Protein: A 3D–QSAR Study, Biochemica et Biophysica Acta., 1039 (1990) 356–366.

(List continued on next page.)

Primary Examiner—Emanuel T. Voeltz
Assistant Examiner—M. Kemper
Attorney, Agent, or Firm—D'Alessandro & Ritchie

[57] ABSTRACT

A method and system for selecting molecules or molecular parts for screening. A base set of molecules on which chemical tests are to be performed is defined, and once defined, the base set may be extended by selecting molecules which are determined to maximize the diversity of the extended set. Diversity of a set of molecules is measured by reference to steric, electrostatic, and hydrogen bonding features of the set of 3D conformational shapes which each molecule in the set may take on. Each molecule is assigned a measure of incremental (added) diversity with respect to the base set of molecules on which chemical tests are to be performed. To do this, for each new molecule, a set of conformations is defined, and for each conformation, a measure of dissimilarity from each conformation of those molecules in the base set is defined. The molecule's measure of added diversity is responsive to a closest match between the any conformation of that molecule and any conformation of any molecule already in the base set. This measure of dissimilarity is determined by means of a continuous function minimization technique, such as gradient descent or simulated annealing. The base set may then be extended with the molecule whose measure of added diversity is greatest.

14 Claims, 5 Drawing Sheets

OTHER PUBLICATIONS

Ghose, et al., Use of Physicochemical Parameters in Distance Geometry and Related There–Dimensional Quantitative Structure–Activity Relationships: A Demonstration Using *Escherichia coli* Dihydrofolate Reductase Inhibitors, Journal of Medical Chemistry, vol. 28, No. 3, 1985, pp. 333–346.

Smellie, et al., Fast Drug–Receptor Mapping by Site–Directed Distances: A Novel Method of Predicting New Pharmacological Leads, J. Chem. Inf. Comput. Sci., vol. 31, No. 3, 1991, pp. 386–392.

Cramer, III et al., Comparative Molecular Field Analysis (COMFA), J. Am. Chem. Soc., vol. 110, No. 18, 1988, pp. 5959–5967.

Crippen, et al., Distance Geometry and Molecular Conformation, Research Studies Press Ltd., 8 Ligand Binding, pp. 361–429.

Hopfinger, A QSAR Investigation of Dihydrofolate Reductase Inhibition by Baker Triazines Based Upon Molecular Shape Analysis, J. Am. Chem. Soc., 1980, 102, 7196–7206.

Doweyko, The Hypothetical Active Site Lattice. An Approach to Modelling Active Sites from Data on Inhibitor Molecules, Journal of American Chemistry, 1988, 31 (7), pp. 1396–1406.

Simon, et al., Mapping of Dihydrofolate–Reductase Receptor Site by Correlation With Minimal Topological (steric) Differences, J. Theor. Biol., 1977, 66, pp. 485–495.

Crippen, Deduction of Binding Site Structure From Ligand Binding Data, Annals New York Academy of Sciences, vol. 439, 1984, pp. 1–11.

Boulu, et al., Voronoi Binding Site Models: Calculation of Binding Modes and Influence of Drug Binding Data Accuracy, Journal of Computational Chemistry, 10 (5), 673–682 (1989).

Crippen, Voronoi Binding Site Models, Journal of Computational Chemistry 8 (7), 943–955 (1987).

Boulu, et al., Voronoi Binding Site Model of a Polycyclic Aromatic Hydrocarbon Binding Protein, J. Med. Chem., 1990, 33, 771–775.

Blankley, Introduction: A Review of QSAR Methodology, Academic Press, Inc., 1983, pp. 1–17.

Nicklaus, et al., QSAR of Conformationally Flexible Molecules: Comparative Molecular Field Analysis of Protein–Tyrosine Kinase Inhibitors, Journal of Computer–Aided Molecular Design, 6 (1992) 487–504.

THREE DIMENSIONAL MEASUREMENT OF MOLECULAR DIVERSITY

CROSS-REFERENCE TO RELATED APPLICATIONS

This application is a continuation-in-part of application Ser. No. 08/382,990, filed Oct. 28, 1994, now U.S. Pat. No. 5,526,281, titled "A Machine-Learning Approach to Modeling Biological Activity for Molecular Design and to Modeling Other Characteristics", and naming inventors David Chapman, Roger Critchlow, Tom Dietterich, Ajay N. Jain, Rick Lathtop, and Tomas Lozano-Perez, which is itself a continuation of application Ser. No. 08/066,389 filed May 21, 1993, now abandoned, having the same title and naming the same inventors. Each of these applications is hereby incorporated by reference as if fully set forth herein.

BACKGROUND OF THE INVENTION

1. Field of the Invention

This invention relates to a three-dimensional approach to measurement of molecular diversity.

2. Description of Related Art

In the art of pharmaceuticals design, it is common to need to survey large numbers of molecular designs, so as to determine what molecular designs are effective for binding to a particular chemical site (such as an enzyme). This is sometimes called "screening" or "lead discovery."

Either whole molecules, portions of molecules, molecular precursors, or side chains could be selected. In combinatorial chemistry, molecular fragments (portions of molecules, molecular precursors, or side chains) are selected, and all or most of the possible combinations of molecular fragments are constructed for actual chemical testing. Thus for example, where there are three sets of side chains, each set having twenty members, the number of cases for a cross-product of the three sets will be about 20×20×20, or eight thousand possible molecules.

In combinatorial chemistry, due to the numerically explosive nature of testing all possible combinations, it is generally necessary to have only a few side chains selected for each library. However, it is also strongly desirable to make these libraries as diverse as possible, so as to widen the search of possible chemical structures and to facilitate the likelihood that something useful will be found. Traditionally, molecules have been selected for screening arbitrarily and with no particular criteria other than to eliminate molecules known to be toxic or have other bad properties. Moreover, the desire to keep libraries "diverse" has been a fairly vague concept with little or no quantification.

An recent article by R. J. Simon et al., in *Techniques in Protein Chemistry IV* (Academic Press: San Diego, 1994), describes a method for maximizing diversity of a set of side chains selected for a library. The described method determines a large number of properties for each candidate side chain, and uses statistical techniques to select a relatively small number of side chains which collectively maximize diversity relative to these properties.

While this method represents an advance over the traditional arbitrary selection of molecules, it has the drawback that it is based on a two-dimensional (2D) formulation of molecule structure. Most bioactive molecules have properties that are responsive to their three-dimensional (3D) structure, and most bioactive molecules that have good binding ability to a particular chemical site have properties that are responsive to the quality of match between the 3D structure of a part of the molecule and the 3D structure of the binding site.

It would be advantageous to select side chains for a screening library responsive to the 3D structure of the molecules, and responsive to 3D properties of the molecule which are known to be correlated with binding ability. However, each molecule typically has a large number of conformations, rotations, and translations ("poses", as described in the parent applications cited herein above); this large number of poses vastly increases the difficulty of actually determining the 3D properties of the molecule and selecting side chains for a screening library responsive thereto.

SUMMARY OF THE INVENTION

The invention provides a method and system for selecting molecules or molecular parts for screening, so as to maximize the diversity of a set of molecules on which chemical tests are to be performed. In a preferred embodiment, a base set of molecules on which chemical tests are to be performed is defined, and once defined, the base set may be extended by selecting molecules which are determined to maximize the diversity of the extended set. Diversity of a set of molecules is measured by reference to steric, electrostatic, and hydrogen bonding features (or other features known to affect molecular binding) of the set of three-dimensional (3D) conformational shapes which each molecule in the set may take on.

In a preferred embodiment, each molecule is assigned a measure of incremental (added) diversity with respect to the base set of molecules on which chemical tests are to be performed. For each new molecule, a set of conformations is defined, and for each conformation, a measure of dissimilarity from each conformation of those molecules in the base set is defined. The molecule's measure of added diversity is responsive to a closest match between any conformation of that molecule and any conformation of any molecule already in the base set. In a preferred embodiment, this measure of dissimilarity is determined by means of a continuous function minimization technique, such as gradient descent or simulated annealing. The base set may then be extended with the molecule whose measure of added diversity is greatest.

In a preferred embodiment, a candidate set of molecules to be added to the base set may be maintained, with each molecule in the candidate set associated with a measure which indicates the estimated added diversity the candidate molecule has with respect to the base set, and sorted by that measure of estimated added diversity. To extend the base set, the candidate molecule with the greatest added diversity is added, after which remaining candidate molecules are tested until one guaranteed to have greatest added diversity is found. This procedure is iterated until a selected condition is reached, such as when the base set has been extended to a selected preferred size.

In a preferred embodiment, the dissimilarity of one conformation of a molecule from another is defined with reference to a degree of spatial overlap of the "best" alignment of the two conformations. The second conformation is repeatedly realigned relative to the first conformation, using a continuous function minimization technique such as gradient descent or simulated annealing, until a best alignment is determined. The dissimilarity is defined responsive to the degree of non-overlap (for selected subsets of atoms) for the best alignment of the two conformations.

In a preferred embodiment, the selection technique is responsive to additional factors indicated by an operator for indicating or contraindicating selection of a molecule, and may also be responsive to interactive operator control. Molecules may be filtered out of consideration responsive to these additional factors either before or after they are determined to best extend the base set. These additional factors include topological similarity to molecules in the base set, known toxic features of the candidate molecule, and interactive approval or disapproval by an operator or coroutine.

In an alternative embodiment, the measure of added diversity of a candidate molecule may be determined responsive to a statistically selected sample subset of conformations, rather than a complete set of conformations. A sample subset of conformations may be selected responsive to a random or pseudorandom variable, a measure of dissimilarity may be determined for each conformation in the subset, and the composite dissimilarity may be estimated in response to the sample subset.

DESCRIPTION OF THE PREFERRED EMBODIMENT

The following description of the invention relies in part on the description of poses and conformations in the parent applications cited herein above (and incorporated by reference). Readers are directed to those disclosures for an extended discussion of poses, conformations, and determination of conformations for a selected molecule.

In the following description, a preferred embodiment of the invention is described with regard to preferred process steps and data structures. However, those skilled in the art would recognize, after perusal of this application, that embodiments of the invention may be implemented using a set of general purpose computers operating under program control, and that modification of a set of general purpose computers to implement the process steps and data structures described herein would not require undue invention.

GENERAL FEATURES OF THE METHOD AND SYSTEM

Figure 1A:
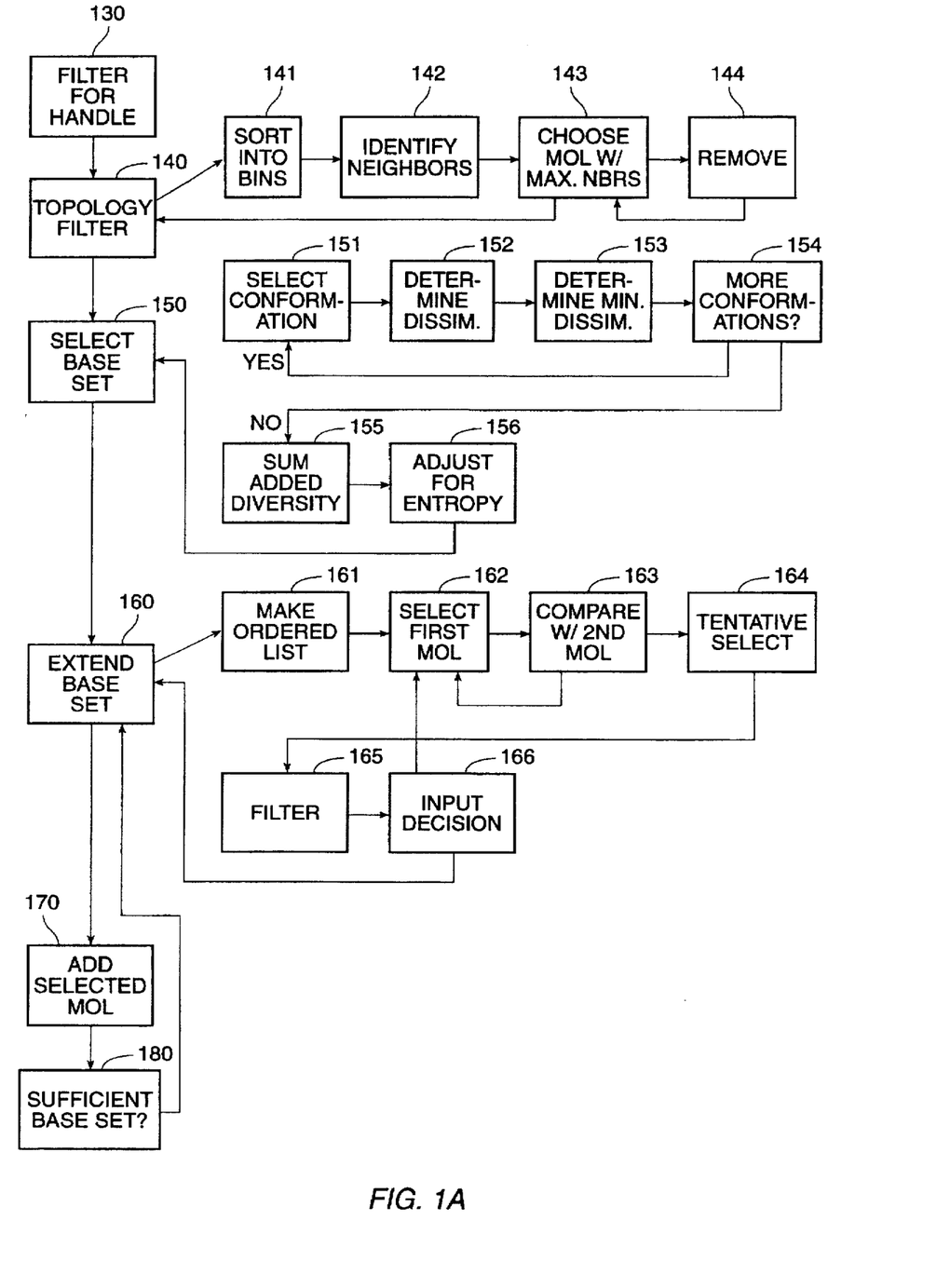
FIG. 1A shows a flow diagram of a method for defining a set of molecules having maximum diversity.
Figure 1B:
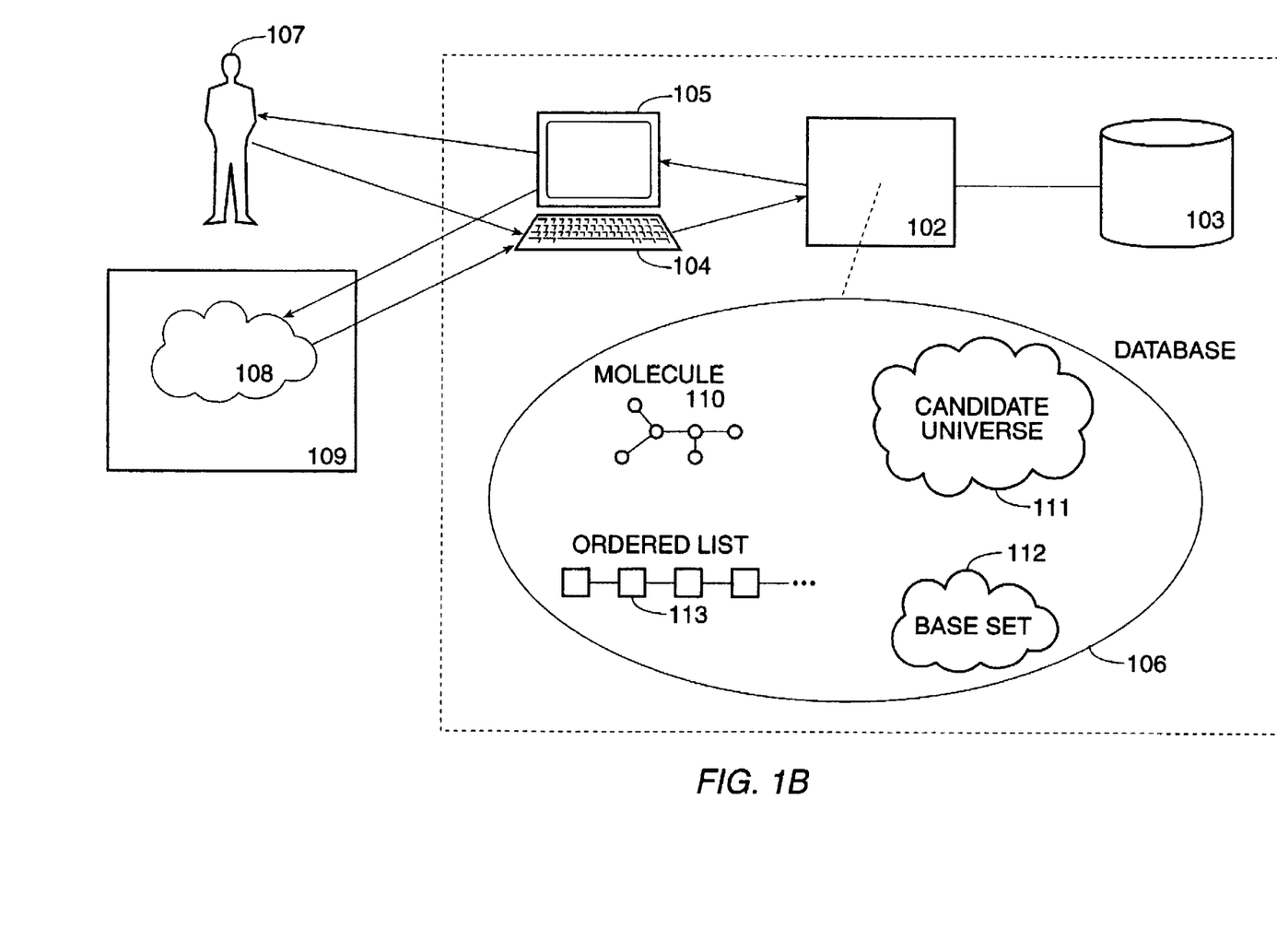
FIG. 1B shows data structures for use with this method. As used herein, "FIG. 1" refers to FIGS. 1A and 1B collectively.

FIG. 1A shows a flow diagram of a method for defining a set of molecules having maximum diversity. FIG. 1B shows data structures for use with this method.

In a preferred embodiment, the invention is used with a general purpose processor 101 having program and data memory 102, mass storage 103, an input device 104 such as a keyboard, mouse, or other pointing device, and an output device such as a display 105, operating under control of application software and accessing a database 106 of molecules and molecular structures. The input device 104 is controlled by, and the output device 105 displays to, an operator 107.

Preferably, the processor 101 comprises a Silicon Graphics "Indigo$^2$" Workstation, having a 150 megahertz Silicon Graphics IP22 chip, a MIPS R4400 processor chip, a MIPS R4010 floating point processor chip, 96 MB of main memory such as RAM (serving as the program and data memory 102), a Silicon Graphics "GU1-Extreme" graphics board, and approximately 1.5 GB of mass memory such as magnetic disk storage (serving as the mass storage 103), or any computing device of similar programming generality. Preferably, the application software operates in conjunction with the IRIX 5.2 operating system software on the preferred processor 101.

The database 106 is preferably stored in the program and data memory 102 and in the mass storage 103, and comprises a set of molecules 110, forming a universe 111 of those molecules 110. As used herein, the term "molecule" refers both to entire molecules and to side chains for construction of molecules.

At a step 130, the processor 101 selects the universe 111 of molecules 110 from a database of known molecules 110, by filtering that database to retain only molecules with a selected "handle". As used herein, the handle for a molecule 110 is an identifiable group of atoms with a known chemical coupling functionality. For example, in the experiment described with FIG. 3, the handle is a carboxy group.

At a step 140, filters the universe 111 to remove those molecules 110 with structure believed to be unacceptable. In a preferred embodiment, molecules 110 known to be likely to be toxic or excessively reactive, or which are known to be likely to misbehave when used as side chains, e.g., by improperly attaching to the main chain, are removed. The remaining candidate universe 111 of molecules 110 is topologically filtered to remove those molecules 110 which are topologically similar.

To perform this step 140, the processor 101 performs the steps 141 through 144 inclusive, and continues with the step 150.

At a step 141, the processor 101 sorts the molecules 110 into a set of bins, where each bin has the same number of atoms of each type, for example, six carbon atoms, one nitrogen atom, and one oxygen atom. Hydrogen atoms are ignored.

At a step 142, the processor 101 identifies, for each molecule 110, all its "neighbor" molecules 110. Two molecules 110 are neighbors if their topological structure differs by either addition or subtraction of a single atom or substitution of a single atom. Hydrogen atoms are ignored. The processor 101 need only look in neighboring bins (bins whose counts differ by only a single addition, subtraction, or substitution) for neighbors (with regard to topological structure) of any particular molecule 110.

At a step 143, the processor 101 identifies the molecule 110 with the greatest number of neighbor molecules 110. If there are no neighbor molecules 110, the method of topological filtering is complete, and the processor 101 continues with the step 150.

In alternative embodiments, the processor 101 may perform the step 143 using the "Tanimoto Coefficient", a measure of topological similarity which is known in the art. In such alternative embodiments, the processor 101 instead identifies the molecule 110 with the greatest number molecules 110 within a selected distance according to the Tanimoto Coefficient.

At a step 144, the processor 101 removes the molecule 110 which had the greatest number of neighbor molecules 110 from the candidate universe 111, updates the count of neighbors for each of that molecule's neighbors, and continues with the step 143.

At a step 150, the processor 101 selects, from the candidate universe 111 of the molecules 110, a base set 112 of molecules 110. To perform this step 150, the base set 112 of molecules 110 may be input from the operator 107 or from a coroutine 108 (the coroutine 108 may comprise another applications program operating on the same processor 101 or another processor 109).

In a preferred embodiment, the processor 101 starts with a null base set 112 and extends this base set 112 by adding a first new molecule 110. Since the method extends the base set 112 by adding the molecule 110 with the greatest incremental (added) diversity, the base set 112 will effectively be initialized with the single molecule 110 with that property. The greatest added diversity to a null base set 112 will be achieved by the single molecule 110 with the greatest interconformational diversity, i.e., the greatest diversity across all its conformations.

The processor 101 determines the added diversity of a molecule 110 by performing the steps 151 through 156 inclusive.

At a step 151, the processor 101 selects a conformation of the molecule 110.

At a step 152, the processor 101 determines the dissimilarity of the selected conformation of the molecule 110 relative to relative to each conformation of each molecule 110 in the base set 112. Dissimilarity is determined using the method described with FIG. 2.

At a step 153, the processor 101 determines the minimum dissimilarity value determined in the step 152. This is the added diversity for the selected conformation of the molecule 110.

At a step 154, the processor 101 determines if there are any further conformations of the molecule 110 for which the added diversity must be determined. If there are further conformations, the processor 101 continues with the step 151. Otherwise, the processor 101 continues with the step 155.

At a step 155, the processor 101 determines the sum of the added diversities determined in the step 154. This sum is the added diversity for the molecule 110. To make this determination, the processor 101 does not actually add the conformations of the molecule 110 to the base set 112; rather, the processor 101 forms a virtual base set 112 in which the conformations of the molecule 110 are sequentially added, and determines the added diversity for each conformation of the molecule 110 in turn. The actual base set 112 is not altered until the processor 101 actually adds the molecule 110 to it.

If the base set 112 is null, the added diversity determined in the steps 151 through 155 inclusive is the interconformational diversity of the molecule 110.

At a step 156, the processor 101 adjusts the added diversity of the molecule 110 for the estimated entropic cost of fixation. Preferably, the adjustment term is equal to a times b, where a is a constant preferably equal to 1.2 kilocalories per mole; and b is the number of rotatable bonds in the molecule 110.

In alternative embodiments, the processor 101 may also adjust the added diversity of the molecule 110 for other estimated entropic costs, such as the entropy of desolvation (i.e., the entropic cost for having the molecule 110 in water).

In alternative embodiments, the processor 101 may determine the added diversity of a molecule 110 by selecting a random or pseudorandom sample of the conformations of the molecule, determining the added diversity of conformations in the pseudorandom sample, and estimating the added diversity of the entire set of conformations using statistical techniques.

At a step 160, the processor 101 selects a single molecule 110 from the candidate universe 111 to extend the base set 112. To perform this step 160, the processor 101 performs the sequence of steps 161 through 166 inclusive, and continues with the step 170.

At a step 161, the processor 101 prepares an ordered list 113 of molecules 110 selected from the candidate universe 111, ordered by their estimated added diversity relative to the base set 112. This step 161 is performed only once, at the time of adding the first new molecule 110. The processor 101 examines each molecule 110 in the candidate universe 111 and determines a value for its interconformational diversity; this value is selected for that molecule's estimated added diversity.

When a molecule 110 is added to the base set 112, the added diversity of any molecule 110 not in the base set 112 is either unchanged or decreased; it cannot be increased. Accordingly, the estimated added diversity recorded for each molecule 110 is always either an accurate value for the added diversity of the molecule 110 (relative to the base set 112), or an overestimate.

At a step 162, the processor 101 selects the first molecule 110 in the ordered list 113, determines its actual added diversity relative to the base set 112, and updates the molecule's estimated added diversity in the ordered list 113 with the molecule's actual added diversity. The molecule's actual added diversity relative to the base set 112 becomes its estimated added diversity relative to later base sets 112.

In a preferred embodiment, to make this determination of the actual added diversity relative to the base set 112, the processor 101 re-performs the steps 151 through 156 inclusive for the molecule 110 relative to the expanded base set 112.

At a step 163, the processor 101 compares the first molecule's actual added diversity (relative to the base set 112) with the second molecule's estimated added diversity. If the first molecule's actual added diversity is now less than the second molecule's estimated added diversity, the processor moves the first molecule 110 to its new proper position on the ordered list 113, and continues with the step 162. Otherwise, the processor 101 continues with the step 164.

At a step 164, the processor 101 tentatively selects the first molecule 110 for extending the base set 112.

At a step 165, the processor 101 filters the selected molecule 110 responsive to additional factors. In a preferred embodiment, the processor 101 displays information about the selected molecule 110, and asks the operator 107 or coroutine 108 to decide whether to accept the selected molecule 110.

At a step 166, the processor 101 inputs the decision result from the operator 107 or coroutine 108. If the selected molecule 110 is rejected, the processor 101 removes the selected molecule 110 from the candidate universe 111, and continues with the step 162. If the selected molecule 110 is accepted, the processor 101 continues with the step 170.

At a step 170, the processor 101 extends the base set 112 by adding the selected molecule 110.

At a step 180, the processor 101 determines if the base set 112 is sufficiently defined. In a preferred embodiment, the base set 112 is sufficiently defined when it reaches a selected size (for example, twenty side chains). However, in alternative embodiments, the base set 112 may be sufficiently defined when the selected molecule's value added diversity is less than a selected threshold, when the base set 112 reaches a selected total diversity, when a selected amount of computation time is reached (for example, one real-time week), or responsive to a combination of some or all of these factors. These selected thresholds may be predetermined, may be selected responsive to the size of the base set 112, responsive to a prior selected molecule's value for added diversity, responsive to the running total diversity of the base set 112, and/or responsive to the amount of computation time used.

If the base set 112 is sufficiently defined, the processor 101 has completed this method; otherwise, it continues with the step 160.

DEFINING THE MEASURE OF DISSIMILARITY

Figure 2A:
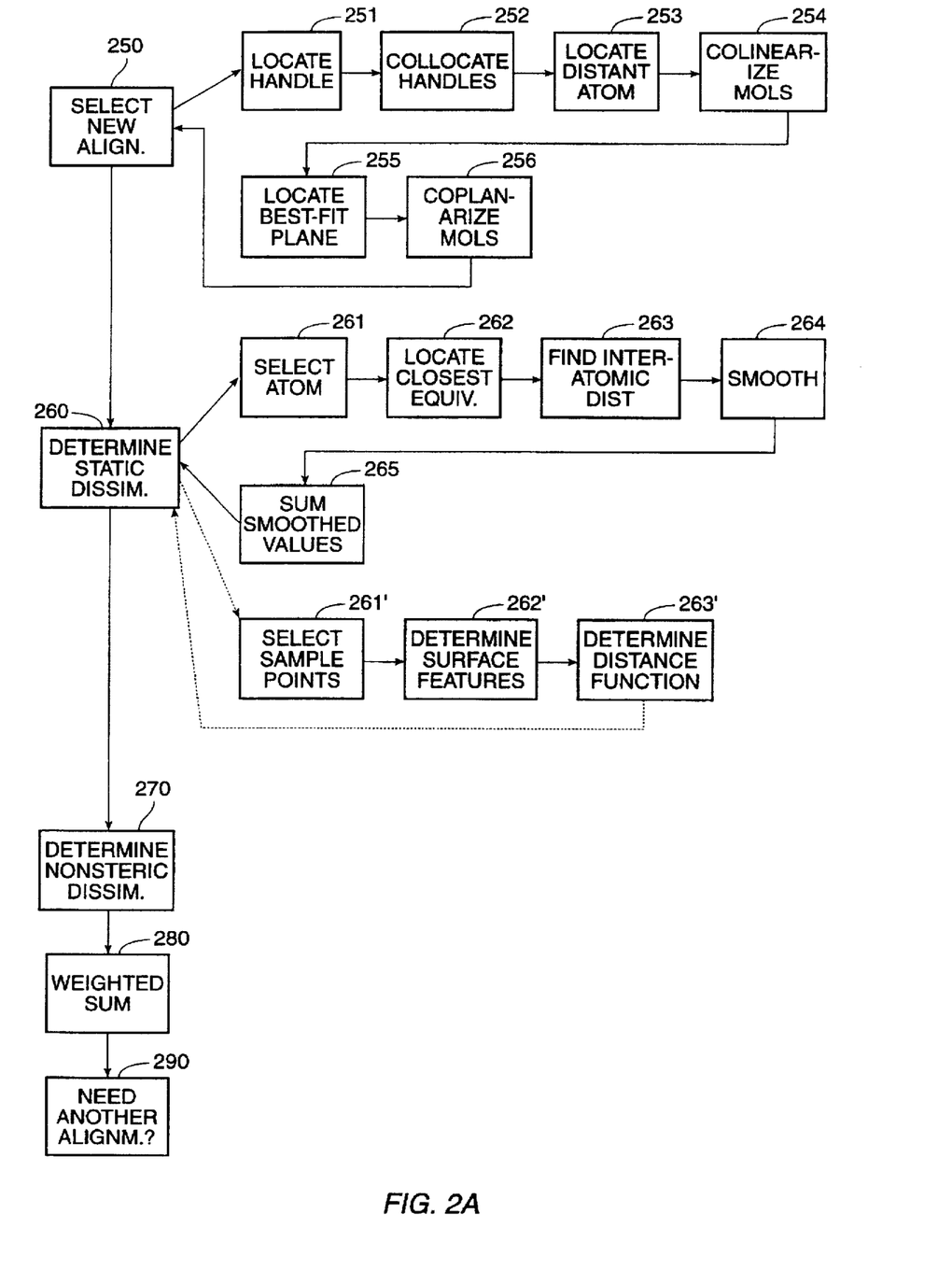
FIG. 2A shows a flow diagram of a method for defining a measure of dissimilarity between two molecules.
Figure 2B:
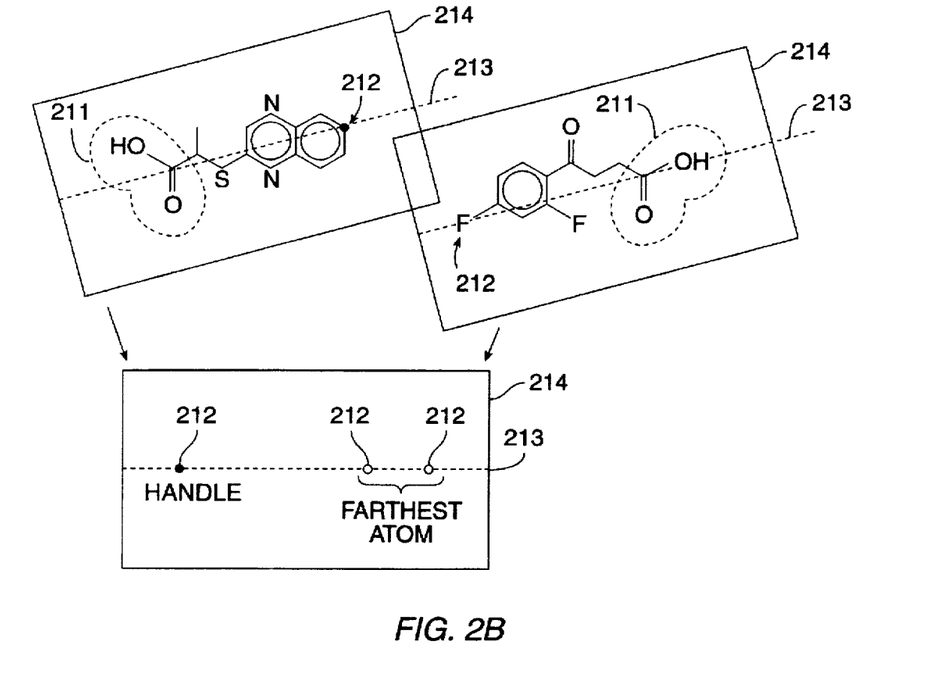
FIG. 2B shows data structures for use with this method.
Figure 2C:
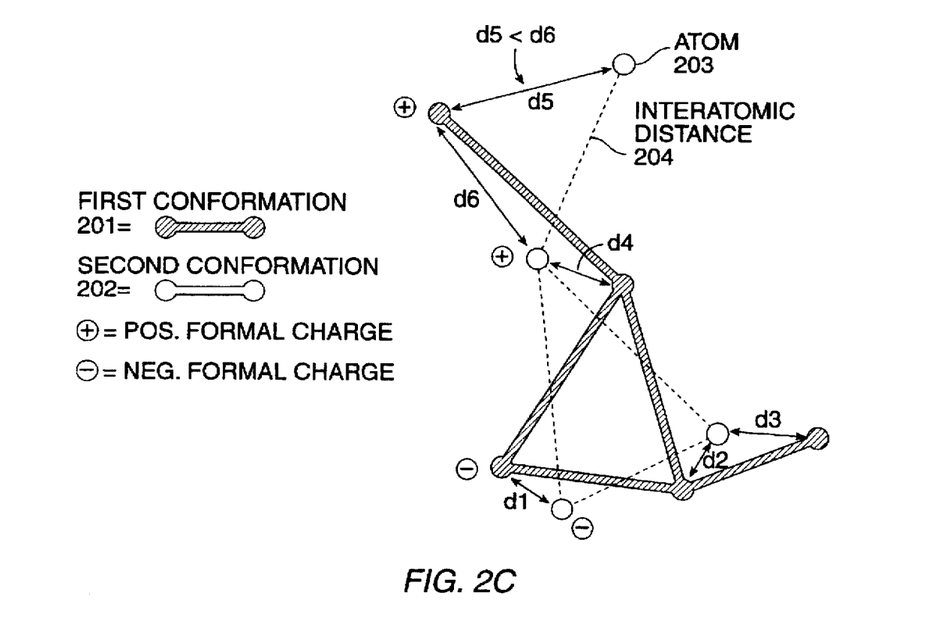
FIG. 2C shows a sample alignment of two molecules for use with this method. As used herein, "FIG. 2" refers to FIGS. 2A, 2B, and 2C collectively.

FIG. 2A shows a flow diagram of a method for defining a measure of dissimilarity between two molecules. FIG. 2B shows data structures for use with this method. FIG. 2C shows a sample alignment of two molecules for use with this method.

In the method of the steps 250 through 290, the processor 101 determines a dissimilarity between a first conformation 201 and a second conformation 202.

At a step 250, the processor 101 selects a new alignment of the second conformation 202 relative to the first conformation 201, by determining a new set of parameters for defining the rotation, translation, and if extant, other pose parameters for defining a pose of the second conformation 202 and positioning it relative to the first conformation 201.

In a preferred embodiment, the processor 101 performs the step 250 for an initial alignment by performing the steps 251 through 256 inclusive, and continues with the step 260.

At a step 251, the processor 101 selects a selected atom 212 in the handle 211 for the two molecules 110. The handle 211 is easily identified because the molecules 110 have been selected from the candidate universe 111 to have that particular handle 211 or coupling functionality. For example, in the experiment described with FIG. 3, the handle 211 comprises a carboxy group, and the selected atom 212 comprises the carbon atom in the carboxy group.

At a step 252, the processor 101 aligns the two molecules 110 to collocate their handles 211.

At a step 253, the processor 101 selects, in each molecule 110, the farthest atom 212 from the handle 211.

At a step 254, the processor 101 aligns the two molecules 110 along a line 213 comprising the collocated handles 211 and the two farthest atoms 212 in each molecule 110. The two farthest atoms 212 are aligned in the same direction from the collocated handles 211. Because the two handles 211 are collocated, there are three points, which the processor 101 makes collinear.

At a step 255, the processor 101 selects a "best-fit" plane 214 for each molecule 110. The best-fit plane 213 is that plane 214 that includes the line 213 that includes the handle 211 and the farthest atom 212, and which has the smallest sum of the squares of distances from atoms 212 in the molecule 110 from the plane 214.

At a step 256, the processor 101 aligns the best-fit plane 214 for each molecule 110, intersecting the two best-fit planes 214 along the line 213 selected in the step 254 and aligning the two best-fit planes 214 to be coplanar. There are exactly two ways to align the two best-fit planes 214 (each best-fit plane 214 may either be normal-up or normal-down); the processor 101 compares these two and chooses the one with the better alignment (i.e., the processor 101 performs the step 260 for each of these two possibilities and chooses the one with the lesser measured dissimilarity).

The method of alignment is then complete and the processor 101 proceeds to the step 260.

At a step 260, the processor 101 determines the steric dissimilarity between the first conformation 201 and the second conformation 202. The processor 101 performs the step 260 by performing the steps 261 through 265 inclusive, and continues with the step 270.

At a step 261, the processor 101 selects an atom 203 in the second conformation 202.

At a step 262, the processor 101 finds the closest corresponding atom 203 in the first conformation 201.

At a step 263, the processor 101 finds the interatomic distance 204 between the first conformation's atom 203 and the second conformation's atom 203.

At a step 264, the processor 101 smoothes the interatomic distance using the smoothing function $$1-\exp(-d^2/k) \qquad (210)$$

where d is the interatomic distance; exp is natural exponential function; and k is a constant preferably equal to 2.0 angstroms (20 nanometers).

This smoothing function is an S-shaped function which penalizes small distances sublinearly and medium distances approximately linearly, and which applies a "soft" threshold to large distances, so that the dissimilarity of two large substitutions is bounded. (As used herein "small", "medium", and "large" distances refer to their relative size on an interatomic scale.) This smoothing yields a metric similar to the Gaussian-overlap similarity measure described in A. C. Good and W. G. Richards, *J. Chem. Inf. Comput. Sci.* 33 (1993), 112–116.

At a step 265, the processor 101 sums the smoothed value for the selected atom 203 with a running total for the second conformation 202, and continues with the step 261 until all atoms 203 in the second conformation 202 have each been selected once.

In a first alternative embodiment, the processor 101 performs the step 260 by performing the steps 261' through 263' inclusive.

At a step 261', the processor 101 selects a set of sampling points like the sampling points detailed in the parent applications cited herein above.

At a step 262', the processor 101 determines the surface features of the first conformation 201 and of the second conformation 202 relative to each sampling point. For example, for steric features, the processor 101 determines a distance, for each sampling point, from the sampling point to an atom 203 in the first conformation 201 and from the sampling point to a corresponding atom 203 in the second conformation 202. This yields a first vector of real distances for the first conformation 201 and a second vector of real distances for the second conformation 201.

At a step 263', the processor 101 determines a distance function between the first vector and the second vector. Preferably, this distance function is the Manhattan distance between the two real vectors (the sum of absolute values of the distance for each vector dimension). However, in alternative embodiments, this distance function may be the ordinary Euclidean distance function between two real vectors, a distance function using another metric, or another type of distance function that varies continuously with the alignment of the molecules 110.

At a step 270, the processor 101 determines a set of nonsteric dissimilarities between the first conformation 201 and the second conformation 202. The processor 101 determines these dissimilarities in like manner as for the step 260, except that instead of selecting every atom 203 (for steric dissimilarity), the processor 101 selects only a subset of atoms 203.

The processor thus determines dissimilarity relative to the following subsets of atoms 203:

uncharged hydrogen bond donors uncharged hydrogen bond acceptors positively formally charged groups of atoms negatively formally charged groups of atoms For example, the processor 101 determines dissimilarity relative to uncharged hydrogen bond donors by performing the steps 261 through 265 inclusive, wherein only those atoms 203 that are uncharged hydrogen bond donors are selected.

In alternative embodiments, the processor 101 may determine dissimilarity relative to other subsets of atoms 203, including:

lipophilic atoms or groups polarizable atoms or groups

In alternative embodiments, the processor 101 may weight the effect of selected atoms 203 on the measure of dissimilarity by giving greater effect to atoms 203 responsive to their characteristics, e.g., atomic size, electronegativity, lipophilicity, polarizability, or other characteristics.

At a step 280, the processor determines a weighted sum of the dissimilarity values determined in the steps 260 and 270. Preferred weights are shown in H.-J. Böhm, *J. Comput.-Aided Mol. Design* 8 (1994) 243–256, or may be as follows:

1.5 for steric dissimilarity 3.0 for uncharged hydrogen donors 3.0 for uncharged hydrogen acceptors 6.8 for positively formally charged groups of atoms 6.8 for negatively formally charged groups of atoms In alternative embodiments, the processor 101 may attempt to determine these weights by examining the results of previous screenings, and in particular by examining the results of relatively small atomic and group substitutions and noting the effect of those substitutions.

At a step 290, the processor 101 determines, using a continuous function minimization technique, if the dissimilarity between the first conformation 201 and the second conformation 202 is large enough to require realignment. For example, with gradient descent, if the magnitude of the gradient of dissimilarity exceeds a selected threshold (such as 0.01 dissimilarity units), the continuous function minimization technique will prescribe that it is large enough to require realignment. If not, the processor 101 has completed this method. Otherwise, the processor 101 continues with the step 250.

The continuous function minimization technique may be any minimization technique used to search for a global extreme value for a continuous function, such as gradient descent or simulated annealing, and is preferably gradient descent. When using gradient descent, the processor 101 repeatedly selects new alignments of the second conformation 201 relative to the first conformation 201 by altering pose parameters of the second conformation 201. The processor 101 seeks to minimize the determined dissimilarity by finding that combination of pose parameters for the second conformation 201 which identify a global minimum of the (continuous) dissimilarity function.

USE OF THE METHOD

Figure 3:
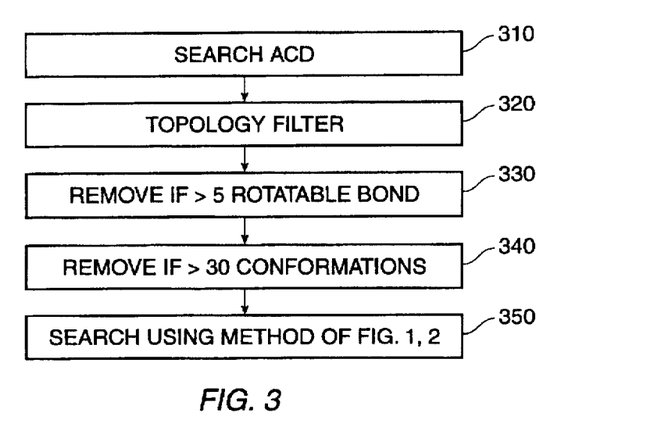
FIG. 3 shows a flow diagram of an experiment involving use of the method to create an example library.

FIG. 3 shows a flow diagram of an experiment involving use of the method to create an example library.

In this example library, side chains are coupled to the main chain with a condensation reaction, requiring a carboxy group on the side chain precursor.

At a step 310, the Available Chemical Directory (ACD) of 143,116 molecules was searched for molecules that both had a single carboxy group, and lacked structural features that might render them toxic or synthetically unsuitable for incorporation into the library. The latter set of structural features were identified and selected prior to filtering the ACD.

At a step 320, the set of molecules found in the step 310 (4961 molecules were found) was filtered topologically, as described herein, to eliminate molecules that differed by only a single atomic substitution.

At a step 330, the set of molecules found in the step 320 (2238 molecules were found) was filtered to remove all molecules that had more than five rotatable bonds.

At a step 340, the set of molecules found in the step 330 was conformationally searched and further filtered to remove all molecules that had more than thirty conformers.

Molecules with more than five rotatable bonds were removed from consideration to aid in conformational searching. This limitation on the flexibility of side chains is chemically reasonable, as the handle to which the side chains are attached is itself highly flexible.

Figure 4:
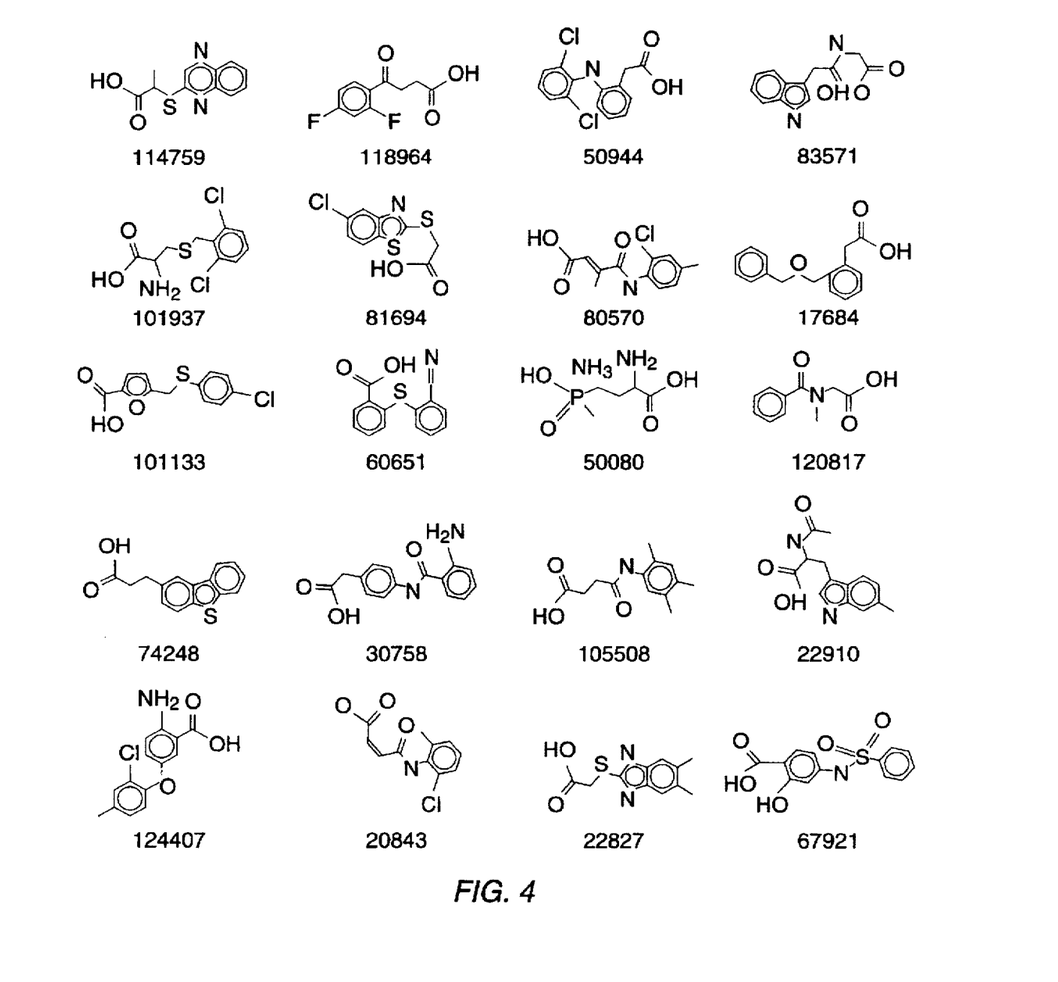
FIG. 4 shows chemical drawings of the molecules found in the experiment described with FIG. 3.

At a step 350, the set of molecules found in the step 340 (1371 molecules were found) was searched using the method described with FIGS. 1A, 1B, 2A, 2B, and 2C, yielding the twenty molecules shown in FIG. 4.

FIG. 4 shows chemical drawings of the molecules found in the experiment described with FIG. 3.

Alternative Embodiments

Although preferred embodiments are disclosed herein, many variations are possible which remain within the concept, scope, and spirit of the invention, and these variations would become clear to those skilled in the art after perusal of this application.

I claim:

1. A system for selecting molecules or molecular parts for screening, comprising a processor having a memory, said memory comprising a candidate universe of molecules and a base set of molecules;

means for directing said processor to define, for each molecule in said candidate universe, a measure of added diversity relative to said base set; and means for directing said processor to select a molecule from said candidate universe for addition to said base set, responsive to said measure of added diversity.

2. A system as in claim 1, comprising a display device coupled to said processor;

means for presenting a description of said selected molecule on said display device;

means for Soliciting input from an operator regarding whether said selected molecule should be added to said base set; and means for determining, responsive to said input, whether or not to add said selected molecule to said base set.

3. A system as in claim 1, comprising means for defining an interconformational diversity of a molecule in said candidate universe.

4. A system as in claim 1, comprising means for determining a conformation of a molecule in said memory;

means for directing said processor to determine a measure of dissimilarity between a first conformation and a second conformation;

wherein said measure of added diversity for a first molecule is responsive to said measure of dissimilarity between conformations of said first molecule and conformations of a molecule in said base set.

5. A system as in claim 4, wherein said means for directing said processor to determine a measure of dissimilarity between a first conformation and a second conformation comprises means for aligning said first conformation and said second conformation;

means for defining a first selected subset of atoms for said first conformation and a second selected subset of atoms for said second conformation;

means for determining, for each atom in said first selected subset, a smoothed distance from an associated atom in said second selected subset; and means for defining a combination of said smoothed distances.

6. A system as in claim 5, wherein said first selected subset and said second selected subset comprise one of: all atoms, uncharged hydrogen donors, uncharged hydrogen acceptors, positively formally charged groups of atoms, negatively formally charged groups of atoms.

7. A system as in claim 5, wherein said first selected subset and said second selected subset comprise one of: relatively electronegative atoms, relatively large atoms, relatively lipophilic atoms, relatively polarizable groups of atoms.

8. A system as in claim 5, wherein said means for aligning comprises means for directing said processor to perform a continuous function minimization technique.

9. A system as in claim 4, wherein said means for directing said processor to determine a measure of dissimilarity between a first conformation and a second conformation is responsive to a measure of non-overlap for selected subsets of atoms for an alignment of said first conformation and said second conformation.

10. A system as in claim 1, comprising means for inhibiting said means for directing said processor to select a molecule from said candidate universe for addition to said base set, said means for inhibiting being responsive to at least one of: a measure of size of said base set, said measure of added diversity for said selected molecule, a measure of total diversity for said base set, a measure of computation time expended by said processor.

11. A system as in claim 1, wherein said base set is a null base set.

12. A system as in claim 1, wherein said means for directing said processor to define, for each molecule in said candidate universe, a measure of added diversity relative to said base set, is responsive to a statistically selected sample subset of conformations of said each molecule.

13. A system as in claim 1, wherein said means for directing said processor to select a molecule from said candidate universe for addition to said base set comprises an list of molecules in said candidate universe, sorted by a measure of estimated added diversity relative to said base set.

14. A system as in claim 1, wherein said means for directing said processor to select a molecule from said candidate universe for addition to said base set is responsive to one of: topological similarity to molecules in the base set, known toxic features of the candidate molecule, interactive approval or disapproval by an operator or coroutine.

* * * * *